United States Patent
Nezami

(10) Patent No.: US 11,890,269 B2
(45) Date of Patent: *Feb. 6, 2024

(54) METHOD OF TREATING CANCER WITH COMBINATIONS OF HISTONE DEACETYLASE INHIBITORS (HDACI) SUBSTANCES

(71) Applicant: Research Cancer Institute of America, Fresno, CA (US)

(72) Inventor: Mohammed Amin Nezami, Clovis, CA (US)

(73) Assignee: Research Cancer Institute of America, Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/223,300

(22) Filed: Apr. 6, 2021

(65) Prior Publication Data

US 2021/0401799 A1 Dec. 30, 2021

Related U.S. Application Data

(63) Continuation of application No. 16/027,146, filed on Jul. 3, 2018, now Pat. No. 10,966,957, which is a continuation of application No. 15/181,169, filed on Jun. 13, 2016, now Pat. No. 10,016,392, which is a continuation of application No. 14/562,507, filed on Dec. 5, 2014, now Pat. No. 9,364,500, which is a continuation of application No. 13/304,630, filed on Nov. 26, 2011, now Pat. No. 8,933,078.

(60) Provisional application No. 61/507,950, filed on Jul. 14, 2011.

(51) Int. Cl.
| | | |
|---|---|---|
| A61K 31/35 | (2006.01) | |
| A61K 31/385 | (2006.01) | |
| A61K 33/00 | (2006.01) | |
| A61K 36/82 | (2006.01) | |
| A61K 38/13 | (2006.01) | |
| A61K 45/06 | (2006.01) | |
| A61K 31/352 | (2006.01) | |
| A61P 35/00 | (2006.01) | |
| A61K 31/192 | (2006.01) | |
| A61G 10/02 | (2006.01) | |
| A61K 31/19 | (2006.01) | |
| A61K 31/22 | (2006.01) | |
| A61K 31/353 | (2006.01) | |
| A61K 38/00 | (2006.01) | |
| A61H 33/14 | (2006.01) | |

(52) U.S. Cl.
CPC .......... *A61K 31/385* (2013.01); *A61G 10/026* (2013.01); *A61K 31/19* (2013.01); *A61K 31/192* (2013.01); *A61K 31/22* (2013.01); *A61K 31/352* (2013.01); *A61K 31/353* (2013.01); *A61K 33/00* (2013.01); *A61K 38/00* (2013.01); *A61K 45/06* (2013.01); *A61P 35/00* (2018.01); *A61H 2033/143* (2013.01)

(58) Field of Classification Search
CPC .. A61K 31/192; A61K 31/352; A61K 31/385; A61K 33/00; A61K 45/06; A61K 2300/00; A61H 2033/143
See application file for complete search history.

(56) References Cited

U.S. PATENT DOCUMENTS

| | | |
|---|---|---|
| 4,569,836 A | 2/1986 | Gordon |
| 6,299,925 B1 | 10/2001 | Xiong et al. |
| 6,376,525 B1 | 4/2002 | Kong |
| 8,933,078 B2 | 1/2015 | Nezami |
| 9,364,500 B2 | 6/2016 | Nezami |
| 9,439,899 B2 | 9/2016 | Proia |
| 10,016,392 B2 | 6/2018 | Nezami |
| 10,966,957 B2 | 4/2021 | Nezami |
| 2003/0103954 A1 | 6/2003 | Rosenbloom |
| 2003/0105031 A1 | 6/2003 | Rosenbloom |
| 2004/0258674 A1 | 12/2004 | Jalili |
| 2006/0035981 A1 | 2/2006 | Mazzio et al. |
| 2006/0057230 A1 | 3/2006 | Chow |
| 2007/0112053 A1 | 5/2007 | Pickett et al. |
| 2007/0190022 A1 | 8/2007 | Bacopoulos et al. |
| 2007/0190114 A1 | 8/2007 | Smart |
| 2008/0305096 A1 | 12/2008 | Verdegem et al. |
| 2010/0239596 A1 | 9/2010 | Lee et al. |
| 2010/0316733 A1 | 12/2010 | Locklear |

(Continued)

FOREIGN PATENT DOCUMENTS

| | | |
|---|---|---|
| CN | 1537161 | 10/2004 |
| CN | 1965715 | 5/2007 |

(Continued)

OTHER PUBLICATIONS

Akbas et al., "The effect of quercetin on topotecan cytotoxicity in MCF-7 and MDA-MB 231 human breast cancer cells." J Surg Res. May 1, 2005;125(1):49-55.

Alleva et al., 2005, α-Lipoic acid supplementation inhibits oxidative damage, accelerating chronic wound healing in patients undergoing hyperbaric oxygen therapy, Biochemical and Biophysical Research Communications, 333:404-410.

(Continued)

*Primary Examiner* — Savitha M Rao

(74) *Attorney, Agent, or Firm* — Knobbe, Martens, Olson & Bear, LLP

(57) ABSTRACT

A method for treating cancer is described using combination therapies comprising the use of hyperbaric oxygen with histone deacetylase inhibitors, with and without glycolytic therapies. The patient is subjected to a hyperbaric environment of substantially pure oxygen. A predetermined dose of one or more HDACI substances is administered to the patient. In addition, glycolitic inhibitors may also be administered. Dosages, pressures, and durations are selected as described herein to have a therapeutic effect on the patient.

7 Claims, No Drawings

(56) References Cited

U.S. PATENT DOCUMENTS

| | | |
|---|---|---|
| 2010/0330087 A1 | 12/2010 | Newell et al. |
| 2011/0104100 A1 | 5/2011 | Riordan et al. |
| 2011/0118309 A1 | 5/2011 | Atadja |
| 2011/0224290 A1 | 9/2011 | Estrela Ariquel et al. |
| 2012/0121730 A1 | 5/2012 | Singh |
| 2012/0269861 A1 | 10/2012 | Sherman et al. |
| 2013/0011488 A1 | 1/2013 | Nezami |
| 2013/0014753 A1 | 1/2013 | Nezami |
| 2013/0129809 A1 | 5/2013 | Srivastava et al. |
| 2015/0366838 A1 | 12/2015 | Lines |
| 2017/0014376 A1 | 1/2017 | Nezami |
| 2017/0020842 A1 | 1/2017 | Elmann |
| 2017/0224654 A1 | 8/2017 | Armstrong et al. |
| 2017/0285027 A1 | 10/2017 | Fantl |
| 2018/0133278 A1 | 5/2018 | Atamaniuk et al. |
| 2019/0125791 A1 | 5/2019 | Wilmotte |
| 2020/0147030 A1 | 5/2020 | Nezami |
| 2020/0206183 A1 | 7/2020 | Nezami |
| 2021/0015787 A1 | 1/2021 | Nezami |
| 2021/0283149 A1 | 9/2021 | Nezami |
| 2022/0087946 A1 | 3/2022 | Nezami |
| 2023/0072294 A1 | 3/2023 | Nezami |

FOREIGN PATENT DOCUMENTS

| | | |
|---|---|---|
| EP | 1 847 274 | 10/2007 |
| JP | 05-070348 | 3/1993 |
| JP | 2006-0298781 | 11/2006 |
| WO | WO 97/47317 | 12/1997 |
| WO | WO 05/023179 | 3/2005 |
| WO | WO 05/083123 | 9/2005 |
| WO | WO 06/059237 | 6/2006 |
| WO | WO 07/121088 | 10/2007 |
| WO | WO 08/011363 | 1/2008 |
| WO | WO 08/082856 | 7/2008 |
| WO | WO 09/019721 | 2/2009 |
| WO | WO 11/112156 | 9/2011 |
| WO | WO 14/091078 | 6/2014 |
| WO | WO 14/111268 | 7/2014 |
| WO | WO 16/054237 | 4/2016 |
| WO | WO 18/170457 | 9/2018 |

OTHER PUBLICATIONS

American Cancer Society, 2019, How chemotherapy drugs work, https://www.cancer.org/content/dam/CRC/PDF/Public/8418.00.pdf, 9 pp.

American Cancer Society, Quercetin, 4 pp., no date.

Amirkhosravi et al., "Pentoxifylline inhibits hypoxia-induced upregulation of tumor cell tissue factor and vascular endothelial growth factor." ThrombHaemost. Oct. 1998;80(4):598-602.

Arce et al., 2006, A proof-of-principle study of epigenetic therapy added to neoadjuvant doxorubiin cyclophosphamide for locally advanced breast cancer, Plos One, 2006, 1(1):e98.

Armeanu et al., "Natural killer cell-mediated lysis of hepatoma cells via specific induction of NKG2D ligands by the histone deacetylase inhibitor sodium valproate" Can Res Jul. 15, 2005 vol. 65 No. 14 pp. 6321-6329.

Bai et al., Jan. 2010, Myricetin and quercetin are naturally occurring co-substrates of cyclooxygenases in vivo, Prostaglandins Leukot Essent Fatty Acids, 82(1):1-11.

Baker et al., "A practical assay of lipoate in biologic fluids and liver in health and disease." Free Radic Biol Med. Sep. 1998; 25(4-5):473-479.

Befon et al., "Continuous Subcutaneous Octreotide in Gastrointestinal Cancer Patients: Pain Control and B-Endorphin Levels", Anticancer Research, 20:4039-4046 (2000) (abstract).

Bettuzzi et al., "Chemoprevention of human prostate cancer by oral administration of green tea catechins in volunteers with high-grade prostate intraepithelial neoplasia: a preliminary report from a one-year proof-of principle study," Cancer Res, Jan. 15, 2006, 66:1234-1240.

Bonnet et al., "A mitochondria-K+ channel axis is suppressed in cancer and its normalization promotes apoptosis and inhibits cancer growth." Cancer Cell. Jan. 2007;11(1):37-51.

Boyd, "Insulin and cancer." Integr Cancer Ther. Dec. 2003, 2(4):315-29.

Cai et al., "Restorative effect of quercetin on subcellular distribution of daunorubicin in multidrug resistant leukemia cell lines K562/ADM and HL-60/ADM." Department of Oncology, Shanghai No. 6 People's Hospital, Shanghai Jiaotong University, Shanghai 200233, P.R. China, Ai Zheng. Dec. 2004;23(12):1611-1615 (abstract).

Cairns et al., "Metabolic targeting of hypoxia and HIF1 in solid tumors can enhance cytotoxic chemotherapy." Proc Natl Acad Sci USA 104: 9445-9450.

Camacho et al., "Phase I dose escalation clinical trial of phenylbutyrate sodium administered twice daily to patients with advanced solid tumors." Invest New Drugs. Apr. 2007;25(2):131-8.

Cao et al., "Dichloroacetate (DCA) sensitizes both wild-type and over expressing Bcl-2 prostate cancer cells in vitro to radiation." Prostate 68: 1223-1231.

Carducci et al., "Phenylbutyrate induces apoptosis in human prostate cancer and is more potent than phenylacetate." Clin Cancer Res. Feb. 1996;2(2):379-87.

Castillo et al., "The effects of the bioflavonoid quercetin on squamous cell carcinoma of the head and neck origin." Am J Surg. 1989;158(4):351-5.

Chang et al., 2006, Reactive oxygen species production is involved in quercetin-induced apoptosis in human hematoma cells, Nutr Cancer, 55(2):201-209 (abstract).

Chen et al., "Quercetin and trichostatin A cooperatively kill human leukemia cells", Pharmazie 60:856-860 (2005).

Chen, L. et al., "Absorption, distribution, elimination of tea polyphenols in rats," Drug Metab Dispos, Sep. 1997, 25(9):1045-1050.

Choi et al., "Mechanism of alpha-lipoic acid-induced apoptosis of lung cancer cells." Ann N Y Acad Sci. Aug. 2009;1171:149-55.

Cruz-Correa et al., Aug. 2006, Combination treatment with curcumin and quercetin of adenomas in familial adenomatous polyposis, Clinical Gastroenterology and Hepatology, 4(8):1035-1038.

Daruwalla et al., "Hyperbaric Oxygen Therapy for Malignancy, A review" World Journal of Surgery, Nov. 2006.

Dashwood et al., "Dietary histone deacetylase inhibitors: From cells to mice to man" Semin Cancer Biol. Oct. 2007, 17(5):363-369.

Dell'Antone, "Inactivation of H+-vacuolar ATPase by the energy blocker 3-bromopyruvate, a new antitumour agent" Life Sci. Oct. 19, 2006;79(21):2049-55.

Dreher et al., "Role of oxygen free radicals in cancer development." Eur J Cancer. Jan. 1996;32A(1):30-38.

Du et al., "Dietary quercetin combining intratumoral doxorubicin injection synergistically induces rejection of established breast cancer in mice." Int Immunopharmacol. Jul. 2010;10(7):819-26.

Du et al., "Quercetin greatly improved therapeutic index of doxorubicin against 4T1 breast cancer by its opposing effects on HIF-1.alpha. in tumor and normal cells." Cancer Chemother Pharmacol. Jan. 2010;65(2):277-87.

Fang et al., "Dietary Polyphenols May Affect DNA Methylation", J. Nutr., Jan. 2007, vol. 137.

Farr, Charles, "The Therapeutic Use of Intravenous Hydrogen Peroxide", A Review, Experimental Evidence of Physiological Effect and Clinical Experience, Nov. 1986, 11 pp.

Ferry et al., "Phase I clinical trial of the flavonoid quercetin: pharmacokinetics and evidence for in vivo tyrosine kinase inhibition." Clin Cancer Res. Apr. 1996;2(4):659-68.

Ganapathy-Kanniappan et al., "3-Bromopyruvate induces endoplasmic reticulum stress, overcomes autophagy and causes apoptosis in human HCC cell lines." Anticancer Res. Mar. 2010;30(3):923-35.

Ganapathy-Kanniappan et al., "3-bromopyruvate: a new targeted antiglycolytic agent and a promise for cancer therapy." Curr Pharm Biotechnol. Aug. 2010;11(5):510-517.

Garcia-Roman et al, "VEGF secretion during hypoxia depends on free radicals-induced Fyn kinase activity in mast cells." Biochem Biophys Res Commun. Oct. 15, 2010;401(2):262-7.

(56) References Cited

OTHER PUBLICATIONS

Gilbert et al., "A phase I dose escalation and bioavailability study of oral sodium phenylbutyrate in patients with refractory solid tumor malignancies." Clinical Cancer Research Aug. 2001, 7:2292-2300.
Glaser KB, "HDAC inhibitors: Clinical update and mechanism-based potential", Biochem Pharmacol (2007).
Gore et al., Apr. 2002, Impact of prolonged infusions of the putative differentiating agent sodium phenylbutyrate on myelodysplastic syndromes and acute myeloid leukemia, Clinical Cancer Research, 8:963-970.
Gore, Steven D. et al., "Combined DNA Methyltransferase and Histone Deacetylase Inhibition in the Treatment of Myeloid Neoplasms," Cancer Res 2006; 66:6361-6369.
Gorospe et al., "Up-regulation and functional role of p21Waf1/Cip1 during growth arrest of human breast carcinoma MCF-7 cells by phenylacetate." Cell Growth Differ. Dec. 1996;7(12):1609-15.
Granowitz et al., "Hyperbaric Oxygen Inhibits benign and malignant human mammary epithelial cell proliferation" Anticancer Res. Nov.-Dec. 2005;25(6B):3833-42.
Grimberg et al., "Role of insulin-like growth factors and their binding proteins in growth control and carcinogenesis." J Cell Physiol. Apr. 2000;183(1):1-9.
Guevara-Aguirre et al., "Growth hormone receptor deficiency is associated with a major reduction in pro-aging signalling, cancer, and diabetes in humans." Sci Transl Med. Feb. 16, 2011;3(70):70ra13.
Han et al., "Effect of glycolytic inhibitors on proliferation and apoptosis of pancreatic cancer cell under hypoxic condition", Chinese Journal of General Surgery, Mar. 2009, 18(3):243-246.
Han, S. et al., "Differentiation of human neuroblastoma by phenylacetate is mediated by peroxisome proliferator-activated receptor gamma," Cancer Res., May 15, 2001, vol. 61:3998-4002.
Haroon et al., "Lung metastatic load limitation with hyperbaric oxygen," Undersee Hyperb Med., Mar.-Apr. 2007, 34(2):83-90.
Hashemzae et al., Aug. 2017, Anticancer and apoptosis-inducing effects of quercetin in vitro and in vivo, Oncology Reports, 38(2):819-828.
Hastak, K. et al., "Role of p53 and NF-kappaB in epigallocatechin-3-gallate-induced apoptosis of LNCaP cells," Oncogene, Jul. 31, 2003, 22:4851-4859.
Hong, J. et al., "Stability, cellular update, biotransformation, and efflux of tea polyphenol (-)-epigallocatechin-3-gallate in HT-29 human colon adenocarcinoma cells," Cancer Res Dec. 15, 2002, 62:7251-7246.
Hsu et al., "Chemoresistance of lung cancer stemlike cells depends on activation of Hsp27." Cancer. Apr. 1, 2011;117(7):1516-28.
Iannitti et al., 2011, Clinical and experimental applications of sodium phenylbutyrate, Drugs, 11(3):227-249.
Ishikawa, A. et al., "Smoking, alcohol drinking, green tea consumption and the risk of esophageal cancer in Japanese men," J Epidemiol, Sep. 2006, 16(5):185-192.
Israel, M. et al., "The metabolic advantage of tumor cells," Mol Cancer, Jun. 7, 2011, 10:70.
Jia et al., "Histone hyperacetylation is involved in the quercetin-induced human leukemia cell death", Pharmazie, 2008, 63:379-383.
Jian, L. et al., "Protective effect of green tea against prostate cancer: a case-control study in southeast China," Int J Cancer, Jan. 1, 2004, 108:130-135.
Jung et al., "EGCG, a major component of green tea, inhibits tumour growth by inhibiting VEGF induction in human colon carcinoma cells," Br J Cancer, Mar. 23, 2001, vol. 84.
Jung et al., "Inhibition of tumour invasion and angiogenesis by epigallocatechin gallate (EGCG), a major component of green tea," Int J Exp Pathol, Dec. 2001, 82:309-316.
Kanadaswami et al., "The antitumor activities of flavonoids." In Vivo. Sep.-Oct. 2005;19(5):895-909.
Kaplan et al., "The Insulin-like Growth Factor Axis and Prostate Cancer: Lessons from the Transgenic Adenocarcinoma of Mouse Prostate (TRAMP) Model 1" Cancer Res May 5, 1999 59; 2203.
Kawada et al., "Insulin-like Growth Factor I Secreted from Prostate Stromal Cells Mediates Tumor-Stromal Cell Interactions of Prostate Cancer" Cancer Res Apr. 15, 2006 66:4419-4425.
Khan et al., "Cancer Chemoprevention Through Dietary Antioxidants: Progress and Promise", Antioxidants and Redox Signaling, vol. 10, No. 3, pp. 475-510, 2008.
Kim et al., "Inhibition of vascular endothelial growth factor induced angiogenesis suppresses tumour growth in vivo" Nature, Apr. 29, 1993, 362:841-844.
Ko et al., "Advanced cancers: eradication in all cases using 3-bromopyruvate therapy to deplete Atp." BiochemBiophys Res Commun. Nov. 5, 2004;324(1):269-275.
Ko et al., "Glucose catabolismin the rabbit VX2 tumor model for liver cancer: characterization and targeting hexokinase," Cancer Lett. Nov. 8, 2001;173(1):83-91.
Koshikawa et al., "Reactive oxygen species generating mitochondrial DNA mutation up regulates hypoxia inducible factor-1 alpha gene transcription via phosphatidylinositol 3-kinase-Akt/protein kinase C/ histone deacetylase pathway" J Biol Chem. Nov. 27, 2009, 284(48):33185-94.
Kurahashi, N. et al., "Green tea consumption and prostate cancer risk in Japanese men: a prospective study," Am J Epidemiol, Jan. 1, 2008, 167(1):71-77.
Kurmasheva et al., "The insulin-like growth factor-1 receptor-targeting antibody, CP-751,871, suppresses tumor-derived VEGF and synergizes with rapamycin in models of childhood sarcoma." Cancer Res. Oct. 1, 2009;69(19):7662-71.
Kurzrock et al., Mar. 7, 2008, Targeted Cancer Therapy, Springer Science & Business Media, p. 362.
Lamson et al., "Antioxidants and Cancer III: Quercetin", Alternative Medicine Review, 5(3):196-208, 2000.
Lee et al., "Role of Bax in quercetin-induced apoptosis in human prostate cancer cells," Biochem Pharmacol. Jun. 15, 2008;75(12):2345-55.
Leroith et al., "The insulin-like growth factor system and cancer." Cancer Lett. Jun. 10, 2003; 195(2):127-37.
Levy, J et al., "Tyrosine protein kinase activity in the DMBA-induced rat mammary tumor: inhibition by quercetin," Biochem Biophys Res Commun., Sep. 28, 1984, 123(3):1227-1233.
Li et al., "Synergistic epigenetic reactivation of estrogen receptor-.alpha. (ER.alpha.) by combined green tea polyphenol and histone deacetylase inhibitor in ER.alpha.-negative breast cancer cells", Molecular Cancer, Biomed Central, Oct. 14, 2010, 9(1):274.
Lin et al., Oct. 1, 2009, A phase I dose-finding study of 5-azacytidine in combination with sodium phenylbutyrate in patients with refractory solid tumors, Clin Cancer Res, 15(19);6241-6249.
Liu et al., "Transcriptional upregulation of TGF-alpha by phenylacetate and phenylbutyrate is associated with differentiation of human melanoma cells." Cytokine. Jul. 1995;7(5):449-56.
Major et al., "The Role of Octreotide in the Management of Patients with Cancer", Ontario Cancer Center, Practice Guideline Report 12-7, Aug. 2004, 37 pp.
Maki, "Small is beautiful: insulin-like growth factors and their role in growth, development, and cancer." J Clin Oncol. Nov. 20, 2010;28(33):4985-95. Epub Oct. 25, 2010.
Martinet et al., "Interpreting clinical assays for histone deacetylase inhibitors." Cancer Manag Res. 2011: 3: 117-141.
Mathupala et al., "Hexokinase II: cancer's double-edged sword acting as both facilitator and gatekeeper of malignancy when bound to mitochondria." Oncogene. Aug. 7, 2006;25(34):4777-86.
Mehrabian, S., "The study of antioxidant and anticarcinogenic green tea and black tea," Pak J Biol Sci, Mar. 15, 2007, 10(6):989-991.
Meng, Studies on the differentiation of human hepatocarcinoma cell induced by historne deacetylase inhibitors and its mechanism, China Doctoral Dissertations Full-Test Database, p. E-072-39.
Michelakis, et al., "Dichioroacetate (DCA) as a potential metabolic-targeting therapy for cancer." Br J Cancer. Oct. 7, 2008;99(7):989-94.
Michelakis, et al., "Metabolic modulation of glioblastoma with dichloroacetate." Sci Transl Med. May 12, 2010;2(31):31ra34.
Millauer et al., "Glioblastoma growth inhibited in vivo by a dominant-negative Flk-1 mutant." Feb. 10, 1994, Nature, 367:576-579.

(56) References Cited

OTHER PUBLICATIONS

Mokrzycki "Anti-atherosclerotic efficacy of quercetin and sodium phenylbutyrate in rabbits", Ann Acad Med Stetin, 2000; 46:189-200 (abstract).
Molnar et al., "Antitumor activity of flavonoids on NK/Ly ascites tumor cells." Neoplasma. 1981;28(1):11-18.
Monneret et al., "Histone deacetylase inhibitors", European Journal of Medicinal Chemistry, Jan. 2005, 40(1):1-13.
Moussa et al., "Hyperbaric oxygen as an adjuvant to cisplatin containing regimen: a companion to a hard journey" Proc Am Soc Clin Oncol 21: 2002 (abstr 2806).
Mukhtar, H. et al., "Tea polyphenols: prevention of cancer and optimizing health," Am J Clin Nutr, Jun. 2000, vol. 71.
Mulholland et al., "Pre-clinical and clinical study of QC12, a water-soluble, pro-drug of quercetin," Annals Oncol Feb. 2001 vol. 12 No. 2 pp. 245-248.
Murray, Quercetin, in How to Prevent and Treat Cancer with Natural Medicine Penguin, Nov. 4, 2003, Health and Fitness, 5 pp.
Mydio et al., "Prostate Cancer: Science and Clinical Practice (Google eBook)", Academic Press, p. 523, Jul. 11, 2003.
Nagano, J. et al., "A prospective study of green tea consumption and cancer incidence, Hiroshima and Nagasaki (Japan),"—Cancer Causes Control, Aug. 2001, 12:501-508.
Nam, S. et al., "Ester bond-containing tea polyphenols potently inhibit proteasome activity in vitro and in vivo," J Biol Chem, Apr. 20, 2001, 276:13322-13330.
Navarro-Peran et al., "The antifolate activity of tea catechins," Cancer Res, Mar. 15, 2005, 65:2059-2064.
Niedzwiecki et al., Sep. 9, 2016, Anticancer efficacy of polyphenols and their combinations, Nutrients, 8(9):1-17.
Nihal et al., "Anti-melanoma effects of vorinostat in combination with polyphenolic antioxidant Epigallocatechin-3-Gallate (EGCG)", Pharmaceutical Research, 27(6):1103-1114, Jun. 2010.
Pedersen PL, "Transport ATPases into the year 2008: a brief overview related to types, structures, functions and roles in health and disease." J Bioenerg Biomembr. Dec. 2007;39(5-6):349-355.
Pedersen, PL, "The cancer cell's "power plants" as promising therapeutic targets: an overview." J Bioenerg Biomembr. Feb. 2007;39(1):1-12.
Pelicano et al., 2008, Glycolysis inhibition for anticancer treatment, Oncogene, 25:4633-4646.
Phuphanich et al., "Oral sodium phenylbutyrate in patients with recurrent malignant gliomas: a dose escalation and pharmacologic study." Neuro Oncol 2005; 7(2):177-182.
Pisters, KM et al., "Phase I trial of oral green tea extract in adult patients with solid tumors," J Clin Oncol, Mar. 15, 2001, 19(6):1830-1838.
Plate et al., "Vascular endothelial growth factor is a potent tumour angiogenesis factor in human gliomas in vivo." Oct. 29, 1992, Nature, 359:845-848.
Pollak et al., "Insulin, insulin-like growth factors, insulin resistance, and neoplasia[1-4]" Am J Clin Nutr. Sep. 2007;86(3):s820-2.
Pollak, "Insulin and insulin-like growth factor signalling in neoplasia." Nat Rev Cancer. Dec. 2008:8(12):915-928.
Pollak, Michael N. et al., "Insulin-like Growth Factors and Neoplasia," Nature Reviews: Cancer, Jul. 2004, 4:505-518.
Prophylaxis, dictionary definition, retrieved on Jun. 25, 2014 from: Vocabulary.com, 4 pp.
Prostate Cancer, Medline Plus, downloaded at http://www.nlm.nih.gov/medlineplus/print/ency/article/000380.htm, Nov. 9, 2009.
Qian et al., "Targeting tumor angiogenesis with histone deacetylase inhibitors: the hydroxamic acid derivative LBH589." Clin Cancer Res. Jan. 15, 2006;12(2):634-42.
Rokes et al., "Sorafenib Plus Valproic Acid for Infant Spinal Glioblastoma," J Pediatr Hematol Concol, Aug. 2010, 32:511-514.
Roomi, MW. et al., "In vivo antitumor effect of ascorbic acid, lysine, proline and green tea extract on human prostate cancer PC-3 xenografts in nude mice: evaluation of tumor growth and immunohistochemistry," In Vivo, Jan.-Feb. 2005, 19:179-184.

Sasabe et al., "Mechanism of HIF-1alpha-dependent suppression of hypoxia-induced apoptosis in squamous cell carcinoma cells." Cancer Sci. Jul. 2005;96(7):394-402.
Scatena et al., "Glycolytic enzyme inhibitors in cancer treatment", Expert Opinion on Investigational Drugs, Informa Healthcare, 17(10):1533-1545, Oct. 2008.
Schwartz et al., "A combination of alpha lipoic acid and calcium hydroxycitrate is efficient against mouse cancer models: preliminary results." Oncol Rep. May 2010;23(5):1407-16.
Selvendiran, "Oxygnation inhibits ovarian tumor growth by downregulating STAT3 and cyclin-D1 expression" Cancer biol Ther, Aug. 2010, 10(4):386-390.
Shabbeer et al., "Focus on Deacetylation for Therapeutic Benefit", IDRUGS, Current Drugs Ltd, Feb. 2005, 8(2):144-154.
Shanafelt, Tait D. et al., "Phase I Trial of Daily Oral Polyphenon E in Patients with Asymptomatic Rai Stage 0 to II Chronic Lymphocytic Leukemia," Journal of Clinical Oncology, Aug. 10, 2009, 27(23):3808-3814.
Shankar, S. et al., "EGCG inhibits growth, invasion, angiogenesis and metastasis of pancreatic cancer," Front Biosci, Jan. 1, 2008, 13:440-452.
Sharma et al., "Molecular pathways in the chemosensitization of cisplatin by quercetin in human head and neck," Cancer BiolTher (2005) 4(9): 949-55.
Shoskes et al., "Quercetin in Men with Category III Chronic Prostatitis: A Preliminary Prospective, Double-Blind, Placebo-Controlled Trial", Urology 54 (6), pp. 960-963, 1999.
Shweiki et al., "Vascular endothelial growth factor induced by hypoxia may mediate hypoxia-initiated angiogenesis." Oct. 29, 1992, Nature, 359:843-845.
Staedler et al., "Drug combinations with quercetin: doxorubicin plus quercetin in human breast cancer cells." Cancer Chemother Pharmacol. Nov. 2011;68(5):1161-1172.
Sun, CL. et al., "Green tea, black tea and breast cancer risk: a meta-analysis of epidemiological studies," Carcinogenesis, Jul. 2006, 27(7):1301-1309.
Sung et al., "Combination of cytotoxic-differentiation therapy with 5-fluorouracil and phenylbutyrate in patients with advanced colorectal cancer." Anticancer Res. Mar.-Apr. 2007;27(2):995-1001.
Suzuki, Y. et al., "Green tea and the risk of breast cancer: pooled analysis of two prospective studies in Japan," Br J Cancer, Apr. 5, 2004, 90:1361-1363.
Takenouchi et al., "Studies on the metabolism of thioctic acid in skin diseases 2. Loading test of thioctic acid in various skin diseases" The Journal of Vitaminology 8, 99-114 (1962).
Tang et al., "The dietary bioflavonoid quercetin synergizes with epigallocathechin gallate (EGCG) to inhibit prostate cancer stem cell characteristics, invasion, migration and epithelial-mesenchymal transition." J Mol Signal. Aug. 18, 2010;5:14.
Tosetti, F., "Angioprevention: angiogenesis is a common and key target for cancer chemopreventive agents," FASEB, J Jan. 2002, vol. 16, 14 pp.
Troy et al., Remington: The Science and Practice of Pharmacy, p. 838, 2006.
Vaupel, "The Role of Hypoxia-Induced Factors in Tumor Progression" Oncologist. 2004;9 Suppl 5:10-17.
Wada et al, "A study on the metabolism of lipoic acid and lipoamide" The Journal of Vitaminology 7, 237-242 (1960).
Wang et al., "Co-treatment with quercetin to enhance the chemopreventive effect of green tea in prostate cancer", FASEB J., Apr. 2010, Meeting Abstract Supplement. Abstract.
Wang et al., Mar. 27, 2012, Quercetin increased the antiproliferative activity of green tea polyphenol (-)-epigallocatechin gallata in prostate cancer cells, Nutrition and Cancer, 64(4):580-587.
Wang, Studies on the apoptosis of NB4 cells induced by histone deacetylase inhibitors in combination with ATRA and As2O3 and its mechanism, China Master's Dissertations Full-Test Database, p. E072-35.
Wardell et al., "Glucose metabolism as a target of histone deacetylase inhibitors." Mol Endocrinol. Mar. 2009;23(3):388-401.
Wenzel et al., "Alpha-Lipoic acid induces apoptosis in human colon cancer cells by increasing mitochondrial respiration with a concomitant O2-*-generation" Apoptosis. Mar. 2005;10(2):359-368.

(56) References Cited

OTHER PUBLICATIONS

Wong et al., "Dichloroacetate induces apoptosis in endometrial cancer cells" Gynecol Oncol 109: 394-1402.
Wu, AH. et al., "Green tea and risk of breast cancer in Asian Americans," Int J cancer, Sep. 10, 2003, 106:574-579.
Xintaropoulou et al., 2008, A comparative analysis of inhibitors of the glycolysis pathway in breast and ovarian cancer cell line models, Oncotarget, 6(27):25677-25695.
Yang et al., "Cancer prevention by tea: animal studies, molecular mechanisms and human relevance," Nat Rev Cancer, Jun. 2009, 9:429-439.
Yang, CS., et al, "Inhibition of carcinogenesis by tea," Annu RevPharmacol Toxicol, 2002, 42:25-54.
Yang, Gong et al., "Prospective Cohort Study of Green Tea Consumption and Colorectal Cancer Risk in Women," Cancer Epidemiol Biomarkers Prev, Jun. 2007, 16:1219-1223.
Yoon, Joo-Heon et al., "Molecular Targets of Dietary Polyphenols with Anti-inflammatory Properties," Yonsei Med J., Oct. 31, 2005, 46(5):585-596.
Zhang et al., "Sodium 4-phenylbutyrate induces apoptosis of human lung carcinoma cells through activating JNK pathway." J Cell Biochem. Nov. 1, 2004;93(4):819-29.
Zhou et al., "Dietary polyphenol quercetin targets pancreatic cancer stem cells." Int J Oncol. Sep. 2010:37(3):551-561.
Alexandrov et al., Aug. 2013, Signatures of mutational processes in human cancer, Nature, 500:415-420.
Ansel et al., 1999, Drug dosage and terminology, in Pharmaceutical Dosage Forms and Drug Delivery Systems, 7th Ed., Lippincott Williams & Wilkins, p. 48.
Arney, Oct. 24, 2014, Coming ever closer—first PARP inhibitor licensed in Europe, Cancer Research UK, https://news.cancerresearchuk.org/2014/10/24/coming-ever-closer-first-part-inhibitor-on-track-to-be-licensed-in-europe, 6 pp.
Azvolinsky, Mar. 16, 2012, MBCC: PARP inhibitors for breast cancer—which subpopulation to target?, https://www.cancernetwork.com/view/mbcc-parp-inhibitors-breast-cancerwhich-subpopulation-target, 3 pp.
Cheng et al., Aug. 31, 1989, The study of green tea extract's anti-tumor effect and mechanism of TPA, Zhonggu Kuangzhan Institute of Technology, 11(4):259-264.
Ciesielski et al., 2020, Epigallocatechin-3-gallate (EGCG) alters histone acetylation and methylation and impacts chromatin architecture profile in human endothelial cells, Molecules, 25:2326.
Harris et al., Oct. 2016, Quercetin as an emerging anti-melanoma agent: a four-focus area therapeutic development strategy, Frontiers in Nutrition, 5(48), 14 pp.
Patnaik et al., Jun. 2019, Drugs targeting epigenetic modifications and plausible therapeutic strategies against colorectal cancer, Frontiers in Pharmacology, 10(588), 15 pp.
Schmutzler et al., 2000, Innovative strategies for the treatment of thyroid cancer, European Journal of Endocrinology, 143:15-24.
Sikora, Sep. 10, 2001, Cancer drug development in the post-genomic age, Current Science, 81(5):549-554.
Taylor, 2017, Synergism of quercetin and sodium butyrate for controlling growth of glioblastoma, Master's thesis, University of South Carolina, retrieved from https://scholarcommons.sc.edu.etd.4149, 102 pp.
Xiao et al., Dec. 31, 1993, University Health Guide, Wubian Dayan Publishing House, 216-217.
Xu et al., Mar. 16, 2015, Enhancing the anti-colon cancer activity of quercetin by self-assembled micelles, International Journal of Nanomedicine, 10:2051-2063.
Zhang, Nov. 15, 2009, Inhibition of glycolysis to the biologic characteristics of pancreatic cancer cell PANC-1 and it mechanism, Kyangyao Health Science and Technology Appraisal, p. 10.
Zheng et al., Feb. 28, 2010, Clinical Biochemical Tests, Zhonggukuang Pharmaceutical Technology Press, pp. 88-90.
Zhou et al., Dec. 31, 1992, Cancer change, abnormal change and sudden change, Research on Cancer Suppressor, 4(2):35-40.
Zips et al., 2005, New anticancer agents; in vitro and in vivo evaluation, In Vivo, 19:1-8.
Baldwin et al., Oct. 1, 2016, Nanoformulation of the PARP inhibitor olaparib enables radiosensitization of a radiation-resistant prostate cancer mode, International J. of Radiation Oncology, Biology, Physics, Poster viewing abstract, 96(2S-Supplement 2016):E595.
Bennouna et al., 2016, Afatinib-based combination regimens for the treatment of solid tumors: rationale, emerging strategies and recent progress, Future Oneal., 12(3):355-372.
Chen et al., 2011, Green tea epigallocatechin gallate enhances therapeutic efficacy of temozolomide in orthotopic mouse glioblastoma models, Cancer Letters, 302:100-108.
Dinarvand et al., 2011, Polylactide-co-glycolide nanoparticles for controlled delivery of anticancer agents, International Journal of Nanomedicine, 6:877-895.
Hu et al., 2016, Pharmacokinetics and antitumor efficacy of DSPE-PET2000 polymeric liposomes loaded with quercetin and tehmozolomide: analysis of their effectiveness in enhancing the chemosensitization of drug-resistant glioma cells, International Journal of Molecular Medicine, 37:690-702.
Lin et al., 2012, Inhibition of mitochondria- and endoplasmic reticulum stress-mediated autophagy augments temozolomide-induced apoptosis in glioma cells, PLOS One, 7(6):e38706.
Nagane, Jan. 2015, Dose-dense temozolomide: is it still promising? Neural. Med. Chir. 55(1):38-49.
Reagan-Shaw et al., Mar. 2007, Dose translation from animal to human studies revisited, The FASEB Journal, 22:659-661.

METHOD OF TREATING CANCER WITH COMBINATIONS OF HISTONE DEACETYLASE INHIBITORS (HDACI) SUBSTANCES

CROSS REFERENCE TO RELATED APPLICATION

This application claims the benefit of U.S. Provisional Application No. 61/507,950 filed Jul. 14, 2011, the entirety of which is hereby incorporated by reference.

FIELD OF INVENTION

This invention relates to the treatment of patients with cancer, particularly cancer in advanced stages through combination therapies comprising the use of hyperbaric oxygen with histone deacetylase inhibitors with and without glycolytic therapies.

BACKGROUND OF THE INVENTION

In 2007, the ten most commonly diagnosed cancers among men in the United States included cancers of the prostate, lung, colon, rectum, and bladder; melanomas of the skin; non-Hodgkins lymphoma; kidney cancer, mouth and throat cancer, leukemia, and pancreatic cancer. In women, the most common cancers were reported as breast, lung and colon cancer. Overall, 758,587 men were told they had cancer and 292,853 men died from cancer in the U.S. in 2007. In women there has been a prevalence of 6,451,737 advanced cases reported by SEER at CDC. In general there were 11,957,599 advanced cancer cases in the US reported in 2010 by CDC and the incidence has been almost unchanged over the previous 8 years (482,000 cases in 2000 versus 456,000 cases in 2008). There has been an annual percentage change of only (−0.6) between years 1999 to 2008 in cancer incidence. Statistics show that deaths caused by advanced cancers from all types have not significantly changed since a decade ago, and in some cases, such as lung cancer with increased incidence since 1930, the death rate has remained rising, especially among women. As more and more chemotherapy agents are introduced to the market for advanced stages of disease, the patient survival rates have remained essentially unchanged. Moreover, the potential toxicity of many chemotherapeutic agents can be a devastating factor both for the clinician and the patient. Therefore the need for non-toxic therapies, used either alone or in combination with traditional chemotherapy, is evident.

Besides chemotherapy agents, many natural and several synthetic medications have been separately assessed to target cancer in different trials. Dichloroacetic acid (DCA), 3 Bromopyruvate (3BP), Sodium phenyl butyrate, and some natural antioxidants such as quercetin as a strong epigenetic modifier and an antioxidant have been used separately in research, and several clinical trials have shown promise in treating patients with advanced cancer either to achieve a response or increase the quality of life. Many of such treatments have been examined and combined with traditional chemotherapies and prove to function as chemosensitizing and radiosensitizing agents increasing their potential effect (1), (2), (3), (13), (46).

SUMMARY OF THE INVENTION

Very generally, the method of the invention comprises administering a predetermined dose of one or more HDACI substances to a patient. The patient is then subjected to a hyperbaric environment of substantially pure oxygen. Dosages, pressures, and durations are selected so as to have a therapeutic effect on the patient.

According to one embodiment of the invention, a predetermined dose of a histone deacetylase inhibitor (HDACI) substance or substances is administered to a patient either intravenously or orally. In particular, sodium phenyl butyrate and quercetin have been found to be useful substances. Within substantially one hour of administering the predetermined substance or substances, the patient is subjected to a hyperbaric environment of substantially pure oxygen at a pressure of substantially one and one half to two atmospheres for a duration of substantially one hour. Preferably, a standard high pressure hyperbaric chamber is used for this step of the method. The predetermined dose is selected as described with more particularity below to have a therapeutic effect upon the patient when used in combination with the hyperbaric environment.

DETAILED DESCRIPTION OF THE INVENTION

Histone Deacetylase Inhibitors

Sodium PhenylButyrate (SPB)

Sodium phenylbutyrate (SPB) is classified by the FDA as an orphan drug for the treatment of urea cycle disorders. Phenylbutyrate (PB) is a prodrug. In the human body, it is metabolized by beta-oxidation to phenylacetate. Phenylacetate conjugates with glutamine to phenylacetylglutamine, that is eliminated with the urine. Phenylbutyric acid (PBA) has growth inhibitory and differentiation-inducing activity in vitro and in vivo in model systems. It stops the cell cycle in its G1-G0 phase. PB is an efficient HDACiand induces apoptosis—probably via c-jun N-terminal kinase (JNK). In lung carcinoma cells, 56 p21waf1-mediated growth arrest in MCF-7 cells, tumor necrosis factor (TNF)-α58 or peroxisome proliferator-activated receptor (PPAR)λ-mediated cell differentiation, and is more potent than phenylacetate in prostate cancer cells, while increasing MHC class I expression (4), (5), (6), (7), (8). PB is converted in vivo into the active metabolite phenylacetate (PA) by β-oxidation in the liver and kidney mitochondria. Most dose-limiting toxicities (DLTs) are fatigue, nausea, and somnolence. Preliminary studies have been conducted in patients with recurrent glioblastoma multiform (GBM) (9). Phase I studies have been conducted in patients with hormone refractory prostate cancers, refractory solid tumor malignancies like colon carcinoma, non-small cell lung cancer (NSCLC), anaplastic astrocytoma, GBM, bladder carcinoma, sarcoma, ovarian carcinoma, rectal hemangiopericytoma, and pancreatic carcinoma, mainly as intravenous infusions but also in AML and myelodysplastic syndrome (MDS)(10). It works by affecting the NF Kappa-B pathway and lowering the inflammatory response and down regulating more than a hundred genes. The optimal dose and place in therapy is yet to be defined, but oral doses up to 36 grams per day have been used with minimal toxicity. In one study (11), 25 percent of patients had stable disease for more than 6 months while on the drug. SPB in oral form is well tolerated and achieves the concentration in vivo that has been shown to have biological activity in vitro. It has been suggested that SPB has a role as a cytostatic agent and should be additionally explored in combination with cytotoxics and other novel drugs. SPB intravenously has been used in advanced solid tumors with a good safety profile (12), (13). However in most studies SPB has been used orally and not intravenously, and certainly has not been combined with other therapies described here including hyperbaric oxygen.

Quercetin

Quercetin is a polyphenyl extracted from apples. Although there is still uncertainty about quercetin's effects against cancer, several mechanisms have been suggested. It has been suggested that quercetin may interact with a variety of cellular receptors, although little evidence is currently available. Mechanisms of cancer treatment suggested by Lamson et al. include inhibition of cellular growth phase at G1 and G2, inhibition of tyrosine kinase to prevent uncontrolled proliferation, influencing estrogen receptors, and interacting with heat shock proteins to prevent proliferation. Regarding cancer prevention, Li et al. have shown that quercetin may interact with receptors like Raf and MEK that are involved in tumor proliferation. Interactions with other receptors are also suspected, mainly affecting expression of surface receptors and growth of cancerous cells. A second theoretical mechanism of cancer prevention is modification of signal transduction. Quercetin is reported to affect cell cycle regulation, cell death, inflammatory reactions and derivation of new blood supply. There is limited in vivo research demonstrating quercetin's ability to treat cancer. One phase 1 clinical trial discussed below has used quercetin to treat a range of advanced cancers in humans. This trial determined an effective dosage for a phase 2 trial, but did not focus on cancer outcome or survival time.

Ferry et al. conducted an open label, uncontrolled dose-finding clinical trial of quercetin as a cancer treatment in 1996. The purpose of this phase 1 trial was to establish a safe dosage for further studies, and thus it was not designed to track cancer progression. In this trial, increasing values of up to 1700 mg/m2 intravenous quercetin were administered for 3 weeks to 50 patients who had cancer deemed no longer treatable by conventional methods. Patients with a variety of cancers were treated including large bowel, stomach, pancreas, ovarian and melanoma. None of the patients achieved suppression as defined by the radiological criteria of WHO, but two showed sustained decreases in unique cancer markers following quercetin therapy (one with metastatic hepatocellular carcinoma, and the other with stage 4 metastatic ovarian cancer that had been previously unresponsive to chemotherapy). In addition, tyrosine kinase levels were measured in 11 subjects, and a decrease in 9 was reported. (Tyrosine kinase may lead to the uncontrolled proliferation of cancer by overriding signals that control cell growth). The authors concluded that this study provides preliminary evidence suggesting quercetin's ability to inhibit tyrosine kinase, and phase 2 studies should be undertaken at doses no higher than 1400 mg/m2 (14). The results of this study have been supported by several in vitro trials in which quercetin caused suppression of tyrosine kinase expression in malignant and non-malignant cells (15).

Two animal studies have been conducted to assess quercetin's ability to treat cancer. One study reported a 20% increase in lifespan after quercetin was injected peritoneally in mice inoculated with acites tumor cells (16). Another study involving mice inoculated with a human squamous cell carcinoma line showed selective inhibition of cancer growth when quercetin was injected interperitoneally, with minimal effects on surrounding normal cells (17). Additional clinical studies are needed to confirm these findings and determine if they are applicable to humans.

It is hypothesized that quercitin can show promising results in treating almost every cancer cell due to its genetic regulatory effects (lowering RAS and bcl-2) and epigenetic effect along with chemo sensitizing effects and estrogen receptor modulation in hormonal dependent tumors. It is also suggested that it has a preventive role in cancer incidence. In one study by Nothlings, U., Murphy, S. P., Wilkens, L. R., Henderson, B. E., Kolonel, L. N. published at American Journal of Epidemiology. 2007; 166(8): 924-31, a total of 529 cases of exocrine pancreatic cancer that arose during the previous 8 years, was tracked through state cancer registries. Quercetin intake was negatively correlated with pancreatic cancer among current smokers, showing a significantly decreased (0.55) relative risk between the highest and lowest quintiles of intake.

There do not, however, appear to be human studies that have looked at quercetin's effects when used intravenously in conjunction with other epigenetic therapies (such as sodium phenyl butyrate).

Lipoic Acid

Lipoic acid (LA) is a cofactor of pyrovate dehydrogenase in Mitochondria. It is not synthetized in human being and is not available in enough quantities in diet or food. Naturally occurring lipoic acid is always covalently bound and not immediately available from dietary sources. Low levels of lipoic acid have been correlated to a variety of disease states (18), (19), (20), (21). A study of LA demonstrated the maximum concentration in plasma and bioavailability are significantly greater than the free acid form, and rivals plasma levels achieved by intravenous administration of the free acid form. Lipoic acid is today considered to be a "conditionally essential nutrient". LA is generally considered safe and non-toxic. RLA is being used in a federally funded clinical trial for multiple sclerosis at Oregon Health and Science University. R-lipoic acid (RLA) is currently being used in two federally funded clinical trials at Oregon State University to test its effects in preventing heart disease and atherosclerosis. Alpha-lipoic acid is approved in Germany as a drug for the treatment of polyneuropathies, such as diabetic and alcoholic polyneuropathies, and liver disease.

More recently the primary effect of lipoic acid is revealed to be not as an in vivo free radical scavenger, but rather an inducer of the oxidative stress response as described below used with hyperbaric oxygen potentiating the oxidation in combination therapy against cancer. It has been shown that Alpha-Lipoic acid induces apoptosis in human colon cancer cells by increasing mitochondrial respiration with a concomitant free oxygen radical generation. Several studies provide evidence that Alpha Lipoic acid can effectively induce apoptosis in human colon cancer cells by a prooxidant mechanism that is initiated by an increased uptake of oxidizable substrates into mitochondria (22).

In 2010, studies have shown great promise in using lipoic acid to treat a variety of cancer cells in mouse syngenic cancer models: MBT-2 bladder transitional cell carcinoma, B16-F10 melanoma and LL/2 Lewis lung carcinoma. Lipoic acid reduced the cell number by 10-50% depending on concentrations. The efficacy of a combination treatment mainly using lipoic acid appeared similar to conventional chemotherapy (cisplatin or 5-fluorouracil) as it resulted in significant tumor growth retardation and enhanced survival. Such preliminary studies suggest a clinical trial is warranted (23).

Lipoic acid decreases cancer cell viability and increases DNA fragmentation of the cells. In general, Lipoic acid's anticancer effect is mediated by induceing apoptosis through caspase-independent and caspase-dependent pathways, which is mediated by intracellular Ca (2+) (24).

Recently there has been a great effort by the pharmaceutical industry to manufacture expensive drugs that have histone deacetylase inhibitory effect. New chemotherapy agents, Hydroxamic derivatives such as LBH 589, and Vorinostat have been suggested to be effective against variety of cancers. It is shown that histone deacetylase inhibitors (HDACI), also inhibit angiogenesis (25). Using lipoic acid and Butyrate in combination can enhance such effect which, independent from their anti apoptotic effect, is considered a new cutting edge method to inhibit metastasis of cancer.

Effects of Hypoxia

Free radicals and Hypoxia can increase the damage to mitochondrial DNA and produce undesirable changes in epigenetics related to risk of cancer growth and metastasis through Hypoxia induced factor one and VEGF. Hypoxia is a common characteristic of locally advanced solid tumors that has been associated with diminished therapeutic response and, more recently, with malignant progression, that is, an increasing probability of recurrence, locoregional spread, and distant metastasis. Emerging evidence indicates that the effect of hypoxia on malignant progression is mediated by a series of hypoxia-induced proteomic and genomic changes activating angiogenesis, anaerobic metabolism, and other processes that enable tumor cells to survive or escape their oxygen deficient environment. The transcription factor hypoxia-inducible factor 1 (HIF-1) is a major regulator of tumor cell adaptation to hypoxic stress. Tumor cells with proteomic and genomic changes favoring survival under hypoxic conditions will proliferate, thereby further aggravating the hypoxia. The selection and expansion of new (and more aggressive) clones, which eventually become the dominant tumor cell type, lead to the establishment of a vicious circle of hypoxia and malignant progression (26). Hypoxia increases tissue factor expression by malignant cells which enhances tumor cell-platelet binding and hematogenous metastasis (27). Hypoxia, whatever its duration, rapidly increases the nuclear content of HIF-1 as well as the mRNA levels of erythropoietin and VEGF. The transcriptional factor hypoxia-inducible factor-1 (HIF-1) plays an important role in solid tumor cell growth and survival. Overexpression of HIF-1alpha has been demonstrated in many human tumors and predicts a poor response to chemoradiotherapy (28).

Hyperbaric Oxygen Therapy

There are studies that suggest that Hyperbaric oxygen therapy (HBOT) can play a positive role in certain malignancies and significantly increase quality of life in patient when used along with chemotherapy(29), inhibit the certain cancer genes and tumor growth in vitro (30),(31), and reduce the tumor burden and restrict the growth of large tumor cell colonies (32). It is possible that this effect is through lowering the hypoxia induced factor one which can change the expression in the VEGF gene subsequently involved in tumor metastasis. VEGF is a major initiator of tumor angiogenesis (33), (34). Furthermore, it is found that VEGF expression is potentiated by hypoxia and that the potentiation of VEGF production in hypoxic areas of solid tumors contributes significantly to VEGF-driven tumor angiogenesis (35), (36).

However hyperoxia as a result of hyperbaric oxygen also produces reactive oxygen species which can damage tumors by inducing excessive oxidative stress (37). On the other hand, free radical related lesions that do not cause cell death can stimulate the development of cancer and can promote cancer growth and metastasis (38) and VEGF exocytosis requires free radicals formation (39). Reactive oxygen species generate mitochondrial DNA mutation and up regulate hypoxia inducible factor-1 alpha gene transcription (40). Therefore reducing oxidative damage is beneficial.

There are available treatments that effectively reduce free radical production and cellular damage. These treatments can potentially modify the epigenetics and increase the effectiveness of other treatments such as DCA and 3 BP. As a result combining HBOT with such modality would offer an advantage to each modality.

In accordance with the invention, the use of HDACI's, administered either orally or intravenously, in combination with HBOT and, optionally, in combination with other modalities described herein, has achieved surprising results in treating various forms of cancer. The results are particularly surprising in connection with advanced cancers as evidenced by the cases described below. Because each patient is different, the specific patient protocol is adjusted to achieve optimal results. However, common to all protocols is the underlying method of the invention as claimed herein.

Optional Strategies

One strategy to destroy or prevent cancers is by targeting their cellular energy production factories. All nucleated animal/human cells have two types of energy production units, i.e., systems that make the "high energy" compound ATP from ADP and P (i). One type is "glycolysis," the other the "mitochondria." In contrast to most normal cells where the mitochondria are the major ATP producers (>90%) in fueling growth, human cancers detected via Positron Emission Tomography (PET) rely on both types of power plants. In such cancers, glycolysis may contribute nearly half the ATP even in the presence of oxygen ("Warburg effect"). Based solely on cell energetics, this presents a challenge to identify curative agents that destroy only cancer cells, as they must destroy both of their power plants causing "necrotic cell death" and leave normal cells alone (41).

Dichloroacetic Acid (DCA)

DCA is a byproduct of chlorinization of water. By stimulating the activity of pyruvate dehydrogenase, DCA facilitates oxidation of lactate and decreases morbidity in acquired and congenital forms of lactic acidosis. The dichloroacetate ion stimulates the activity of the enzyme pyruvate dehydrogenase by inhibiting the enzyme pyruvate dehydrogenase kinase. Thus, it decreases lactate production by shifting the metabolism of pyruvate from glycolysis towards oxidation in the mitochondria.

Cancer cells change the way they metabolize oxygen in a way that promotes their survival. Solid tumors, including the aggressive primary brain cancer glioblastomamultiforme, develop resistance to cell death, in part as a result of a switch from mitochondrial oxidative phosphorylation to cytoplasmic glycolysis. DCA depolarizes mitochondria, increases mitochondrial reactive oxygen species, and induces apoptosis in glycolytic cancer cells, both in vitro and in vivo. DCA therapy also inhibits the hypoxia-inducible factor-1alpha, promoted p53 activation, and suppressed angiogenesis both in vivo and in vitro (42). There is substantial evidence in preclinical in vitro and in vivo models that DCA might be beneficial in human cancer (43), (44), (45). Furthermore, as predicted, activating mitochondria by DCA increases oxygen consumption in the tumor and dramatically enhances the effectiveness of hypoxia-specific chemotherapies in animal models (46). In laboratory studies of isolated cancer cells grown in tissue culture, DCA restores the original metabolism, and promotes their self-destruction. This has led to the use of DCA for treating cancer, by individuals experimenting with it themselves, by doctors administering it to patients, by scientists testing it in cancer tissue cultures in cell culture and in mice, and in human Phase II studies. A phase one study published in January 2007 by researchers at the University of Alberta, who had tested DCA on cancer cells grown in mice, found that DCA restored mitochondrial function, thus restoring apoptosis, allowing cancer cells to self-destruct and shrink the tumor. Akbar and Humaira Khan have, since 2007, treated cancer patients using DCA off-label at their private clinic, Medicor Cancer Centres, in Toronto. They have treated several types of cancer and revealed that some patients "are showing varied positive responses to DCA including tumor shrinkage, reduction in tumor markers, symptom control, and improvement in lab tests." DCA has improved certain biochemical parameters, but it has not demonstrated improved survival. The mitochondria-NFAT-Kv axis and PDK are important therapeutic targets in cancer; the orally available DCA is a promising selective anticancer agent (47). However there are no studies in literature in regards to using DCA intravenously to maximize its effect when combined with other treatments such as 3 BP or SPB intravenously.

3 Bromopyruvate (3BP)

3-bromopyruvate (3BP), a hexokinase inhibitor, lowers the ATP production in cancer cell and has shown great promise in animal studies either used as intra arterial or intratumoral injection. 3-bromopyruvate (3-BrPA), a lactic acid analog, has been shown to inhibit both glycolytic and mitochondrial ATP production in rapidly growing cancers (48), leave normal cells alone, and eradicate advanced cancers (19 of 19) in a rodent model (49). Recent research in tumor metabolism has uncovered cancer-cell-specific pathways that cancer cells depend on for energy production. 3-bromopyruvate (3-BrPA), a specific alkylating agent and potent ATP inhibitor, has been shown both in vitro and in vivo to disrupt some of these cancer-specific metabolic pathways, thereby leading to the demise of the cancer cells through apoptosis. As an alkylating agent and a potent inhibitor of glycolysis, it has recently been exploited to target cancer cells, as most tumors depend on glycolysis for their energy requirements. The anticancer effect of 3-bromopyruvate is achieved by depleting intracellular energy (ATP) resulting in tumor cell death. The principal mechanism of action and primary targets of 3-bromopyruvate, and the impressive antitumor effects of 3-bromopyruvate in multiple animal tumor models, have been discussed recently. The primary mechanism of 3-bromopyruvate is via preferential alkylation of GAPDH. 3-bromopyruvate mediates cell death linked to generation of free radicals. Research also has revealed that 3-bromopyruvate induces endoplasmic reticulum stress and inhibits global protein synthesis, further contributing to cancer cell death. Therefore, studies reveal the tremendous potential of 3-bromopyruvate as an anticancer agent (50).

Also there is interest in researching transport ATPase that has seen tremendous progress. These ATPases driven in reverse by a proton gradient have the capacity to interconvert electrochemical energy into mechanical energy and finally into chemical energy conserved in the terminal bond of ATP (51). It is suggested that 3BP inactivates H+-vacuolar ATPase, the enzyme that makes certain compartments in the cell acidic. Inactivation probably involves alkylation of the enzyme on a thiol group, essential for H+-ATPase activity for dithiothreitol secured complete protection from 3-Br PA inactivation. The findings are discussed with regards to a possible involvement of lysosome destabilization in 3-Br PA induced cell death (52). Studies at Johns Hopkins University (53) and (54) recently have shown efficacy and dose related response when 3 BP is used as even a single therapy, when used intraarterially. However, its role in more aggressive cancers as a solo treatment is not supported. Also its intravenous application has not caused tumor regression due to lower concentration at the target site. However, if used intravenously, combined with other therapies described here, a different scenario results. This may theoretically be due to an additive or synergistic effect on Mitochondria.

Octreotide

Octreotide (brand name Sandostatin,) is an octapeptide that mimics natural somatostatin pharmacologically, though it is a more potent inhibitor of growth hormone, glucagon, and insulin than the natural hormone. Octreotide is absorbed quickly and completely after subcutaneous application. Maximal plasma concentration is reached after 30 minutes.

Oncogenes express proteins of "Tyrosine kinase receptor pathways", a receptor family including insulin or IGF-Growth Hormone receptors. Other oncogenes alter the PP2A phosphatase brake over these kinases. Octreotide has been used in variety of medical conditions since 1979. Since it inhibits secretion of insulin and also acts as a suppressing agent for Insulin growth factor one (IgF1), its use has been suggested in a variety of Glycolytic cancers. Octreotide is found to have therapeutic application beneficial to patients as shown by experiments on animals (55).

GH hormone induces in the liver, the synthesis and release of insulin like growth factor (IGF). The latter activates, like insulin, the IGF-tyrosine kinase receptors (IGFR), triggering the MAP kinase-ERK mitogenic signal. In normal physiology GH stimulates a triglyceride lipase in adipocytes, increasing the release of fatty acids and their β oxidation. In parallel, OH would close the glycolytic source of acetyl CoA, perhaps inhibiting the hexokinase interaction with the mitochondria. This effect, which renders apoptosis possible, does not occur in tumor cells.

GH mobilizes the fatty acid source of acetyl CoA from adipocytes, which should help the formation of ketone bodies. But since citrate synthase activity is elevated in tumors, ketone bodies do not form. Hence, butyrate cannot inhibit histone deacetylase (HDAC), the enzyme cuts acetylated histone tails, this will silence several genes like PETEN, P53, or methylase inhibitory genes. Therefore combining the histone deacetylase inhibitors with Octreotide can have a significant additive effect on glycolytic tumors.

There appears to be a correlation between IgF1 receptors and the behavior of the cancer cell. The surface distribution of IGF-IGFR may determine if a cell is sterile or endowed with a mitotic potential (55). Therefore, using octreotide along with other combination therapies can potentially change the cancer cellular motivation to differentiate. Finally, the recent discovery of a population of Dwarfs with no GH receptors, which does not develop cancers, illustrates the GH/IGF prediction, establishing a link between ancient and recent biochemical observations on tumors (56).

Finally there are studies that have suggested a correlation between both the cancer risk as well as the cancer prognosis with the serum IgF-1 level in human (57). For example observations implicate IGF-I as an important factor during the initiation and progression of primary prostate cancer and provide evidence that there is a strong selection against expression of IGF1R and IGF2R in metastatic and androgen-independent disease (58), (59). Growing links between insulin and the etiology as well as prognosis in colon, prostate, pancreatic, and, particularly, breast cancer are reviewed. Of particular concern is the evidence that elevated IGF-1 may interfere with cancer therapy, adversely affecting prognosis (60).

Octreotide used in protocols described below demonstrates the effectiveness of such treatment in lowering the IgF-1 significantly.

EXAMPLES

Based on above facts, such substances have been employed using Intravenous and oral targeted therapies to reduce anabolic glycolysis in patients with cancer along with epigenetic treatments with HDACI and hyperbaric oxygen. These treatments can increase quality of life and can improve the patient survival. More particularly, an integrative cancer care/approach was undertaken to treat patients who referred for such intervention voluntarily. As of October 2011, 40 patient charts were selected randomly and reviewed. The inclusion criteria were diagnosis of cancer. No patients were excluded. Patients were aged 27 to 83 years. All were diagnosed by their oncologist/physician and were offered standard conventional treatment of surgery, traditional chemotherapy or radiation. Out of 40 patients 20 of them refused standard care or there was no conventional option available for them due to severity of the disease. Out of 40 patients, 23 of them had advanced stage disease with micro or macro multiple metastasis at the time of referral, before starting the treatment. 19 of these patients (47 percent) had already been treated with multiple chemotherapy agents unsuccessfully and had progression or recurrence of disease manifested by their tumor markers or scans.

The patients were managed based on unique developed protocols that were designed in correlation with available research studies and clinical trials that implicate using specific natural and synthetic IV therapies. IV therapies are targeted at epigenetic level and consist of antioxidants, quercetin, DCA, sodium phenyl butyrate, and lipoic acid separately or in combination. All patients received one or more of such treatments, The most effective synergistic combination was found to be intravenous sodium phenyl butyrate and quercetin. Doses of each treatment remained the same or close on each treatment, Quercetin was given intravenously at the dose 0.5 to 1.0 gram (50 mg/ml). When administered, SPB was dosed at 5 to 10 gram (25 to 50 ml of 200 mg/ml, When administered, DCA was dosed at 500 mg to 6 gram (maximum 100/kg) When administered, lipoic acid was given at 600-1000 mg, Hyperbaric oxygen treatment was applied, with standard 1.5 to 2.0 atmosphere pressure for 45-90 minutes (average 60 minutes) on each session. When administered octreotide was given subcutaneously at 50-400 mcgs.

All patients started the program after educating them about their possible options of conventional and non conventional treatments and consents obtained. The progression of disease was measures during the course of treatment through tumor markers, Imaging studies and markers for cancer growth, necrosis, LDH, and inflammation, CRP, as well as the Natural killer cell activity or lymphocyte count and Circulatory tumor cells.

The following results were obtained during or after completing the course of therapy:
1) Subjective Increase in QOL (increase energy level, less pain scores and elevation in mood: 100 percent
2) Immunological response: Increase in Natural Killer cell activity or WBC count: 35% of patients had initial low NK/WBC, all these patients have increased NK activity after therapy
3) Potential decrease in tumor activity by measuring LDH: 40 percent of patients had high LDH, ALL these patients have shown decreased LDH after the therapy
4) Response in Tumor markers, enough to qualify for clinical response: 50 percent
5) Shrinkage of tumor in radiographic studies: 35 percent
6) Decrease in CRP (correlation with improved survival): 23 percent
7) Decrease in IgF-1: 12 percent of these patients had increased IgF-1, suggested to correlate with prognosis in literature. All these patients had improved IgF-1 after the treatment Since patients with cancer may have significant stratifying confounders in selecting their control group, we used each patient's pre interventional status as the control arm. Patients other stratifying confounders did not change during the study.

Results:
1) These data reveals superior response in the group of patients compared to the controls. In 47 percent of patients treated there was no conventional option available at the time of referral. In this group results are far better compared to conventional modalities of treatment. (no treatment option available)
2) Patients who received both HBOT and IV therapies did better as far as their imaging, their quality of life and tumor shrinkage as well as controlling their tumor markers than the ones who did the IV therapies only.
3) Patients with stage four terminal disease receiving the above program, exceeded response beyond the standard of care expectations, and the patients who did receive chemotherapy concurrently with above targeted therapies had significant improvement in quality of life and chemotherapy response.

CONCLUSION

In an integrative cancer care program that combines hyperbaric oxygen therapy with specific Intravenous antioxidants and epigenetic modifications, along with intravenous and/or oral DCA and 3BP, patient survival as well as quality of life improved significantly. The above described modality of care was found to be superior to conventional standards of care. The exact reasons for this are still uncertain, but could possibly be due to the conjunctive effect on the cancer cell mitochondria.

REFERENCES

1) Role of Bax in quercetin-induced apoptosis in human prostate cancer cells. Lee D H, Szczepanski M, Lee Y J.
Source: Department of Surgery and Pharmacology, School of Medicine, University of Pittsburgh, Pittsburgh, PA 15213, USA.

2) Restorative effect of quercetin on subcellular distribution of daunorubicin in multidrug resistant leukemia cell lines K562/ADM and HL-60/ADM.
Cai X, Chen F Y, Han J Y, Gu C H, Zhong H, Ouyang R R.
Source: Department of Oncology, Shanghai No. 6 People's Hospital, Shanghai Jiaotong University, Shanghai 200233, P.R. China. caixuncn@yahoo.com.cn 3) Molecular pathways in the chemosensitization of cisplatin by quercetin in human head and neck
Cancer BiolTher (2005) 4: 949-55.
H Sharma, S Sen, N Singh 4) Sodium 4-phenylbutyrate induces apoptosis of human lung carcinoma cells through activating JNK pathway.
J Cell Biochem. 2004 Nov. 1; 93(4):819-29.
Zhang X, Wei L, Yang Y, Yu Q.
Source: Pulmonary Center, Department of Medicine, Boston University Medical Center, Boston, Massachusetts 02118, USA.

5) Up-regulation and functional role of p21Waf1/Cip1 during growth arrest of human breast carcinoma MCF-7 cells by phenylacetate.
Cell Growth Differ. 1996 December; 7(12):1609-15.
Gorospe M, Shack S, Guyton K Z, Samid D, Holbrook NJ.
Source: Laboratory of Cellular and Molecular Biology, Gerontology Research Center, National Institute on Aging, NIH, Baltimore, Maryland 21224, USA.

6) Transcriptional upregulation of TGF-alpha by phenylacetate and phenylbutyrate is associated with differentiation of human melanoma cells.
Liu L, Hudgins W R, Miller A C, Chen L C, Samid D.
Source: Clinical Pharmacology Branch, National Cancer Institute, Bethesda, MD 20892, USA.

7) Differentiation of human neuroblastoma by phenylacetate is mediated by peroxisome proliferator-activated receptor gamma.
Cancer Res. 2001 May 15; 61(10):3998-4002.
Han S, Wada R K, Sidell N.
Source: Department of Gynecology and Obstetrics, Emory University School of Medicine, 1639 Pierce Drive, Atlanta, GA 30322, USA.

8) Phenylbutyrate induces apoptosis in human prostate cancer and is more potent than phenylacetate.
Clin Cancer Res. 1996 February; 2(2):379-87.
Carducci M A, Nelson J B, Chan-Tack K M, Ayyagari S R, Sweatt W H, Campbell P A, Nelson W G, Simons J W.
Source: The Johns Hopkins Oncology Center and The Brady Urological Institute, Baltimore, Maryland 21205, USA 9) Oral sodium phenylbutyrate in patients with recurrent malignant gliomas: a dose escalation and pharmacologic study.
Neuro Oncol 2005; 7(2):177-182
Phuphanich S, Baker S D, Grossman S A, Carson K A, Gilbert M R, Fisher J D, Carducci M A.
Source: The New Approaches to Brain Tumor Therapy CNS Consortium, Winship Cancer Institute, Emory University, Atlanta, GA 30322, USA. s_phuphanich@emoryhealthcare.org 10) Interpreting clinical assays for histone deacetylase inhibitors.
Cancer Manag Res. 2011; 3: 117-141.
Martinet N, Bertrand P.
Source: Laboratory of Bioactive Molecules, Institute of Chemistry, University of Nice—Sophia Antipolis, Parc Valrose, Nice, France;
Published online 2011 May 9. doi: 10.2147/CMR.S9661 PMCID: PMC3101110

11) A phase I dose escalation and bioavailability study of oral sodium phenylbutyrate in patients with refractory solid tumor malignancies.
Clinical cancer Research August 2001, 7/2292
Gilbert J, Baker S D, Bowling M K, Grochow L, Figg W D, Zabelina Y, Donehower R C, Carducci M A.
Source: Division of Medical Oncology, Department of Oncology, The Johns Hopkins University School of Medicine, 1 M88 Bunting-Blaustein Cancer Research Building, 2650 Orleans Street, Baltimore, MD 21231-1000, USA.

12) Phase I dose escalation clinical trial of phenylbutyrate sodium administered twice daily to patients with advanced solid tumors.
Invest New Drugs. 2007 April; 25(2):131-8. Epub 2006 Oct. 20.
Camacho L H, Olson J, Tong W P, Young C W, Spriggs D R, Malkin M G.
Source: Department of Medicine, Memorial Sloan-Kettering Cancer Center, Joan and Sanford I. Weill Medical College of Cornell Medical Center, New York, New York, USA.

13) Combination of cytotoxic-differentiation therapy with 5-fluorouracil and phenylbutyrate in patients with advanced colorectal cancer.
Anticancer Res. 2007 March-April; 27(2):995-1001.
Sung M W, Waxman S.
Quercetin Source: Division of Hematology-Oncology, Department of Medicine, Box 1129 Mount Sinai School of Medicine, One Gustave L. Levy Place, New York, New York 10029, USA. max.sung@mssm.edu 14) Phase 1 clinical trial of the flavonoid: Pharmacokinetics and evidence for in vivo tyrosine kinase inhibition. Clinical Cancer Research. 1996; 2:659-68.
Ferry D R, Smith, A., Malkhandi, J., Fyfe, D. W., deTakats, P. G., Anderson, D., Baker, J., Kerr, D. J.

15) Tyrosine protein kinase activity in the DMBA-induced rat mammary tumor: inhibition by quercetin.human colon cancer cell lines and in primary colorectal tumors.
BiochemBiophys Res Commun. 1984 Sep. 28; 123(3):1227-33.
Levy J, Teuerstein, I., Marbach, M., Radian, S., Sharoni, Y.

16) Antitumor activity of flavonoids on NK/Ly ascites tumor cells.
Neoplasma. 1981; 28(1):11-8.
Molnar J, Beladi, I., Domonkos, K., Foldeak, S., Boda, K., Veckenstedt, A.

17) The effects of the bioflavonoid quercetin on squamous cell carcinoma of the head and neck origin.
Am J Surg. 1989; 158(4):351-5.
Castillo M H, Perkins, E., Campbell, J. H., Doerr, R., Bassett, J. M., Kandaswami, C., Middleton, E. Jr.

18) A practical assay of lipoate in biologic fluids and liver in health and disease.
Baker H, Deangelis B, Baker E R, Butner S H.
Free Radic Biol Med. 1998 September; 25(4-5):473-9.
Source: Department of Preventive Medicine and Community Health, University of Medicine & Dentistry of New Jersey, New Jersey Medical School, Newark 07107, USA.

19) "Studies on the metabolism of thioctic acid in skin diseases. II. Loading test of thioctic acid in various skin diseases".
Journal of Vitaminology 8: 99-114. PMID 13984665. Takenouchi, K, Aso, K, Kawashima, S (June 1962).
20) "A study on the metabolism of lipoic acid and lipoamide". Journal of Vitaminology 7: 237-42. PMID 140040. Wada, M, Shigeta, Y, Inamori, K (September 1961).
21) Study on the Serum Level of Thioctic Acid in Patients with Various Diseases. J Vitaminology. (1961) 7:48-52 Shigeta Y, Hiraizumi G, Wada M, Oji K, Yoshida T.
22) Alpha-Lipoic acid induces apoptosis in human colon cancer cells by increasing mitochondrial respiration with a concomitant O2-*-generation
Apoptosis. 2005 March; 10(2):359-68.
Wenzel U, Nickel A, Daniel H. Molecular Nutrition Unit, Department of Food and Nutrition, Technical University of Munich, Hochfeldweg 2, D-85350, Freising, FRG. uwenzel@wzw.turn.de
23) A combination of alpha lipoic acid and calcium hydroxycitrate is efficient against mouse cancer models: preliminary results.
Oncol Rep. 2010 May; 23(5):1407-16.
Schwartz L, Abolhassani M, Guais A, Sanders E, Steyaert J M, Campion F, Israël M. Service de Radiothérapie Hôpital Pitié-Salpétrière, bd. de l'Hôpital, 75013 Paris, France. laurent.schwartz@polytechnique.edu
24) Mechanism of alpha-lipoic acid-induced apoptosis of lung cancer cells.
Ann N Y Acad Sci. 2009 August; 1171:149-55.
Choi S Y, Yu J H, Kim H.
Department of Food and Nutrition, Brain Korea 21 Project, Yortsei University College of Human Ecology, Seoul, Korea.
25) Targeting Tumor Angiogenesis with Histone Deacetylase Inhibitors: the Hydroxamic Acid Derivative LBH589
doi: 10.1158/1078-0432.CCR-05-1132 Clin Cancer Res Jan. 15, 2006 12; 634
26) The Role of Hypoxia-Induced Factors in Tumor Progression
Institute of Physiology and Pathophysiology, University of Mainz, Mainz, Germany Correspondence: Peter Vaupel, M.D., Dr. Med., M.A., Institute of Physiology and Pathophysiology, University of Mainz, Duesbergweg 6, 55099 Mainz, Germany
27) Pentoxifylline inhibits hypoxia-induced upregulation of tumor cell tissue factor and vascular endothelial growth factor.
ThrombHaemost. 1998 October; 80(4):598-602.
Amirkhosravi A, Meyer T, Warnes G, Amaya M, Malik Z, Biggerstaff J P, Siddiqui F A, Sherman P, Francis J L.
Source: Cell Biology, Hemostasis and Thrombosis Research Unit, Walt Disney Memorial Cancer Institute at Florida Hospital, Orlando 32804, USA.Ali_Amirkhosravi@mail.fhmis.net
28) Mechanism of HIF-1alpha-dependent suppression of hypoxia-induced apoptosis in squamous cell carcinoma cells.
Cancer Sci. 2005 July; 96(7):394-402. Sasabe E, Tatemoto Y, Li D, Yamamoto T, Osaki T.
Source: Department of Oral Oncology, Kochi Medical School, Kochi University, Kohasu, Oko-cho, Nankoku-city, Japan.
29) Efficacy of pre and post Hyperbaric oxygen as an adjuvant to cis platinum containing regimen,
Proc, American Society of Clinical Oncology 21: 2002 (abstr 2806)
30) Oxygnation inhibits ovarian tumor growth by down-regulating STAT3 and cyclin-D1 expression Cancer biol Ther, August 2010
Selvendiran, Karuppaiyah, Dept of Internal Medicine and Comprehensive Cancer Center, Ohio State Univ. Columbus, OH, USA
31) Hyperbaric Oxygen Inhibits benign and malignant human mammary epithelial cell proliferation, Granowitz E V, Tonomura N, Benson R M
Dept of Medicine BayState Medical Center, Tuft University School of Medicine, Springfield, MA 01199, USA
32) Lung Metastatic loan limitation with hyperbaric oxygen UHM 2007, Vol 34, No. 2-HBO2 and lung metastasis
ABU T. M. PATEL. A. B. Almehdi Department of pharmacology, University of South Alabama College of Medicine, Mobile, AL 36688
33. Inhibition of vascular endothelial growth factor induced angiogenesis suppresses tumour growth in vivo Kim, K. J., Li, B., Winer, J., Armanini, M., Gillett, N., Phillips, H. S., and Ferrara, N. (1993). Nature (London) 362, 841-844[Medline]
34. Glioblastoma growth inhibited in vivo by a dominant-negative Flk-1 mutant. Millauer, B., Shawver, L. K., Plate, K. H., Risau, W., and Ullrich, A. (1994) Nature (London) 367, 576-579[Medline]
35. Vascular endothelial growth factor induced by hypoxia may mediate hypoxia-initiated angiogenesis. Shweiki, D., Itin, A., Soffer, D., and Keshet, E. (1992) Nature (London) 359, 843-845[Medline]
36. Vascular endothelial growth factor is a potent tumour angiogenesis factor in human gliomas in vivo. Plate, K. H., Breier, G., Weich, H. A., and Risau, W. (1992) Nature (London) 359, 845-848[Medline]
37) Hyperbaric Oxygen Therapy for Malignancy, A review World Journal of Surgery, November, 2006
JurstineDaruwalla, B. Sc, Chris Christophi, MD,
38) Role of oxygen free radicals in cancer development.
Eur J Cancer. 1996 January; 32A(1):30-8.
Dreher D, Junod A F.
Source: Respiratory Division, Geneva University Hospital, Switzerland.
39) VEGF secretion during hypoxia depends on free radicals-induced Fyn kinase activity in mast cells.
Epub 2010 Sep. 17.
BiochemBiophys Res Commun. 2010 Oct. 15; 401(2):262-7.
Sasabe E, Tatemoto Y, Li D, Yamamoto T, Osaki T.
Source: Department of Oral Oncology, Kochi Medical School, Kochi University, Kohasu, Oko-cho, Nankoku-city, Japan.
40) Reactive oxygen species generating mitochondrial DNA mutation up regulates hypoxia inducible factor-1 alpha gene transcription via phosphatidylinositol 3-kinase-Akt/protein kinase C/histone deacetylase pathway
J Biol Chem. 2009 Nov. 27, 284(48):33185-94. Epub 2009 Oct. 1
41) The cancer cell's "power plants" as promising therapeutic targets: an overview.
J BioenergBiomembr. 2007 February; 39(1):1-12.
Pedersen P L.
Source: Department of Biological Chemistry, Johns Hopkins University, School of Medicine, 725 North Wolfe Street, Baltimore, Maryland 21205-2185, USA. ppederse@jhmi.edu 42) Dichloroacetate (DCA) as a potential metabolic-targeting therapy for cancer
SciTransl Med. 2010 May 12; 2(31):31ra34.
ED Michelakis*,1, L Webster1 and J R Mackey
Department of Medicine, University of Alberta, Edmonton, Canada; 2Department of Oncology, University of Alberta, Edmonton, Canada
Metabolic modulation of glioblastoma with dichloroacetate.
Michelakis E D, Sutendra G, Dromparis P, Webster L, Haromy A, Niven E, Maguire C, Gammer T L, Mackey J R, Fulton D, Abdulkarim B, McMurtry M S, Petruk K C.
43) A mitochondria-K+ channel axis is suppressed in cancer and its normalization promotes apoptosis and inhibits cancer growth
Cancer Cell 11: 37-51
Bonnet S, Archer S L, Allalunis-Turner J, Haromy A, Beaulieu C, Thompson R, Lee C T, Lopaschuk G D, Puttagunta L, Bonnet S, Harry G, Hashimoto K, Porter C J, Aridrade M A, Thebaud B, Michelakis E D (2007).
44) Dichloroacetate induces apoptosis in endometrial cancer cells
Gynecol Oncol 109: 394-402
Wong J Y, Huggins G S, Debidda M, Munshi N C, De Vivo I (2008).
45) Dichloroacetate (DCA) sensitizes both wild-type and over expressing Bcl-2 prostate cancer cells in vitro to radiation.
Prostate 68: 1223-1231
Cao W, Yacoub S, Shiverick K T, Namiki K, Sakai Y, Porvasnik S, Urbanek C, Rosser C J (2008)
46) Metabolic targeting of hypoxia and HIF1 in solid tumors can enhance cytotoxic chemotherapy.
Proc Natl Acad Sci USA 104: 9445-9450
Cairns R A, Papandreou I, Sutphin P D, Denko N C (2007)
47) A Mitochondria-K+ Channel Axis Is Suppressed in Cancer and Its Normalization Promotes Apoptosis and Inhibits Cancer Growth
Sébastien Bonnet1, Stephen L. Archer1, 2, Joan Allalunis-Turner3, Alois Haromy1, Christian Beaulieu4, Richard Thompson4, Christopher T. Lee5, Gary D. Lopaschuk5, 6, Lakshmi Puttagunta7, Sandra Bonnet1, Gwyneth Harry1, Kyoko Hashimoto1, Christopher J. Porter8, Miguel A. Andrade8, Bernard Thebaud1, 6 and Evangelos D. Michelakis
48) Glucose catabolism in the rabbit VX2 tumor model for liver cancer: characterization and targeting hexokinase
Ko et al., Cancer Letts., 173, 83-91, 2001
Volume 173, Issue 1, Pages 83-91 (8 Nov. 2001)
Young Hee Koa, Peter L. Pedersena, J. F. Geschwindb
Received 11 May 2001; received in revised form 26 Jun. 2001; accepted 28 Jun. 2001.
49) Advanced cancers: eradication in all cases using 3-bromopyruvate therapy to deplete ATP. BiochemBiophys Res Commun. 2004 Nov. 5; 324(1):269-75.
Ko Y H, Smith B L, Wang Y, Pomper M G, Rini D A, Torbenson M S, Hullihen J, Pedersen P L. The Russell H. Morgan Department of Radiology, Johns Hopkins University School of Medicine, Baltimore, MD 21205-2185, USA. yko@jhmi.edu
50) 3-bromopyruvate: a new targeted antiglycolytic agent and a promise for cancer therapy. Curr Pharm Biotechnol. 2010 August; 11(5):510-7.
Ganapathy-Kanniappan S, Vali M, Kunjithapatham R, Buijs M, Syed L H, Rao P P, Ota S, Kwak B K, Loffroy R, Geschwind J F.
Source: Russell H. Morgan Department of Radiology and Radiological Sciences, Johns Hopkins University School of Medicine, Baltimore, MD 21287, USA.
51) Transport ATPases into the year 2008: a brief overview related to types, structures, functions and roles in health and disease.
J BioenergBiomembr. 2007 December; 39(5-6):349-55.
Pedersen P L., Source: Department of Biological Chemistry, Johns Hopkins University, School of Medicine, 725 North Wolfe Street, Baltimore, MA 21205-2185, USA. ppederse@jhmi.edu
52) Inactivation of H+-vacuolar ATPase by the energy blocker 3-bromopyruvate, a new antitumour agent
P. Dell'Antone, a, Department of Experimental and Biomedical Sciences, University of Padova, Padova, Italy
Received 29 Mar. 2006; accepted 29 Jun. 2006. Available online 5 Jul. 2006.
53) 3-Bromopyruvate induces endoplasmic reticulum stress, overcomes autophagy and causes apoptosis in human HCC cell lines.
Ganapathy-Kanniappan S, Geschwind J F, Kunjithapatham R, Buijs M, Syed L H, Rao P P, Ota S, Kwak B K, Loffroy R, Vali M.
Source: Russell H. Morgan Department of Radiology and Radiological Sciences, Johns Hopkins University School of Medicine, 600 N. Wolfe Street, Blalock Building, Room 545, Baltimore, MD 21287, USA.
54) Hexokinase II: cancer's double-edged sword acting as both facilitator and gatekeeper of malignancy when bound to mitochondria.
Oncogene. 2006 Aug. 7; 25(34):4777-86.
Mathupala S P, Ko Y H, Pedersen P L.
Source: Department of Neurological Surgery and Karmanos Cancer Institute, Wayne State University School of Medicine, Detroit, MI, USA.
55) The metabolic advantage of tumor cells
Maurice Israel and Laurent Schwartz
Molecular Cancer Volume 10
Av Aristide Briand 2, Bures sur Yvette 91440, France, LIX: Ecole Polytechnique Palaiseau 91128 and Hôpital Raymond Poincaré, 104 Bd Raymond Poincaré Garches 92380m, France
56) Growth hormone receptor deficiency is associated with a major reduction in pro-aging signalling, cancer, and diabetes in humans. Guevara-Aguirre J, Balasubramanian P, Guevara-Aguirre M, Wei M, Madia F, Cheng C W, Hwang D, Martin-Montavalvo A, Ingles S, de Cabo R, Cohen P, Longo V D:
57) Insulin, insulin-like growth factors, insulin resistance, and neoplasia
Am J Clin Nutr September 2007 vol. 86 no. 3 820S-821S
Michael N Pollak, Prostate Cancer Foundation, US Army, National Cancer Institute of Canada, the National Cancer Institute (USA), and the Canadian Breast Cancer Research Alliance.
58) The Insulin-like Growth Factor Axis and Prostate Cancer: Lessons from the Transgenic Adenocarcinoma of Mouse Prostate (TRAMP) Model 1
Cancer Res May 5, 1999 59; 2203
Paula J. Kaplan, Subburaman Mohan, Pinchas Cohen, Barbara A. Foster, and Norman M. Greenberg2
59) Insulin-like Growth Factor I Secreted from Prostate Stromal Cells Mediates Tumor-Stromal Cell Interactions of Prostate Cancer
Cancer Res Apr. 15, 2006 66; 4419
Manabu Kawada, Hiroyuki Inoue, Tohru Masuda, and Daishiro Ikeda 60) Insulin and cancer.
Integr Cancer Ther. 2003 December; 2(4):315-29.
Boyd D B.
Source: 239 Glenville Road, Greenwich, CT 06831, USA. dbb@integrativeoncology.org

What is claimed is:

1. A method for treating a patient having cancer, the method comprising:
   administering a predetermined dose of one or more HDACI substances to the patient; and,
   subjecting the patient to a hyperbaric pressure environment of substantially pure oxygen;
   said predetermined dose, hyperbaric pressure, and the duration of said subjection being selected to have a therapeutic effect on said cancer.

2. The method of claim 1, wherein said duration is substantially one hour.

3. The method of claim 1, wherein said hyperbaric pressure is substantially between one and one half to two atmospheres.

4. The method of claim 1, wherein the subjecting step is carried out within about one hour from the administering step.

5. The method of claim 1, wherein the HDACI substance is selected from the group consisting of sodium phenyl butyrate, quercetin, lipoic acid; and combinations thereof.

6. The method of claim 1, further comprising administering a therapeutic amount of one or more substances selected from the group consisting of DCA, 3BP, and octreotide.

7. The method of claim 1, wherein said dose is administered either orally or intravenously or both.

* * * * *